US005766574A

United States Patent [19]
Christina-Beck et al.

[11] Patent Number: 5,766,574
[45] Date of Patent: Jun. 16, 1998

[54] DUAL COMPONENT TOOTH WHITENING DENTIFRICE

[75] Inventors: Lisa M. Christina-Beck, Burlington; John P. Curtis, Bloomsbury; Susan E. Greenfeder, Metuchen; Richard Theiler, Bridgewater, all of N.J.

[73] Assignee: Colgate Palmolive Company, New York, N.Y.

[21] Appl. No.: 746,728

[22] Filed: Nov. 15, 1996

Related U.S. Application Data

[60] Provisional application No. 60/008,389, Dec. 8, 1995.

[51] Int. Cl.$^6$ .............. A61K 7/16; A61K 7/20; A61K 31/375; A61K 33/40
[52] U.S. Cl. .............. 424/53; 424/49; 424/613; 424/616
[58] Field of Search ............... 424/49–58, 613, 424/616

[56] References Cited

U.S. PATENT DOCUMENTS

| | | |
|---|---|---|
| 3,976,223 | 8/1976 | Jass et al. |
| 4,528,180 | 7/1985 | Schaeffer |
| 4,976,955 | 12/1990 | Libin ............ 424/53 |
| 4,988,500 | 1/1991 | Hunter et al. ............ 424/53 |
| 5,000,942 | 3/1991 | Libin ............ 424/53 |
| 5,122,365 | 6/1992 | Murayama ............ 424/53 |
| 5,171,564 | 12/1992 | Nathoo et al. ............ 424/53 |
| 5,240,415 | 8/1993 | Haynie ............ 424/53 |
| 5,256,402 | 10/1993 | Prencipe et al. ............ 424/53 |
| 5,264,205 | 11/1993 | Kelly ............ 424/53 |
| 5,279,816 | 1/1994 | Church et al. ............ 424/53 |
| 5,401,495 | 3/1995 | Murayama ............ 424/53 |
| 5,565,190 | 10/1996 | Santalucia et al. ............ 424/53 |
| 5,597,554 | 1/1997 | Wagner ............ 424/53 |
| 5,599,525 | 2/1997 | Hsu et al. ............ 424/53 |
| 5,599,527 | 2/1997 | Hsu ............ 424/53 |
| 5,614,174 | 3/1997 | Hsu et al. ............ 424/53 |
| 5,631,000 | 5/1997 | Pellico et al. ............ 424/53 |
| 5,648,064 | 7/1997 | Gaffar et al. ............ 424/53 |

FOREIGN PATENT DOCUMENTS 0202359  11/1986  European Pat. Off. ......... A61K 7/20

*Primary Examiner*—Shep K. Rose
*Attorney, Agent, or Firm*—Paul Shapiro

[57] ABSTRACT

A dual component whitening dentifrice composition is disclosed which comprises a first dentifrice component containing a peroxide compound such as urea peroxide and a second dentifrice component containing an abrasive such as alumina or silica which is incompatible with the peroxide, the first and second dentifrice components being maintained separate from the other until dispensed and combined for application to teeth requiring whitening.

24 Claims, No Drawings

DUAL COMPONENT TOOTH WHITENING DENTIFRICE

BACKGROUND OF THE INVENTION

FIELD OF THE INVENTION

This invention relates generally to preparations for whitening human teeth, and more particularly, to a stable, dual component dentifrice composition which when applied onto the surface of teeth exhibits heightened whitening of teeth.

Many substances that a person confronts or comes in contact with on a daily basis can "stain" or reduce the "whiteness" of one's teeth. In particular, the foods, tobacco products and beverages such as tea and coffee that one consumes tend to stain one's teeth. These products tend to accumulate on the enamel layer of the tooth and form a pellicle film over the teeth. These staining and discoloring substances can then permeate the enamel layer. This problem occurs gradually over many years, but imparts a noticeable discoloration of tooth enamel. The majority of the population consider clean, white teeth to be aesthetically desirable. Dull-looking, stained teeth are objectionable to most people both on the basis of cosmetic appearance and also socially as an indication of poor oral hygiene.

Dentifrices, especially toothpaste, gels and powders containing active oxygen or hydrogen peroxide liberating ingredients such as hydrogen peroxide, urea peroxide and peroxides, percarbonates and perborates of alkali and alkaline earth metals have been disclosed in the prior art for whitening teeth.

The most widely used tooth whitening agents are hydrogen peroxide and urea peroxide. One method in current practice for whitening teeth used by dental professionals involves the use of 37% hydrogen peroxide in combination with heat and light to promote the whitening action. This method, although effective, is losing favor with dental professionals because clinical and scientific evidence indicates that high concentrations of peroxide can cause irritation of oral tissue.

Another professional method for whitening teeth involves the use of peroxy generating compounds such as urea peroxide (carbamide peroxide) at concentrations of 10–20% to achieve the desired whitening effect. Urea peroxide rapidly breaks down into hydrogen peroxide due to the water present in saliva. This whitening method known as an office-monitored at-home bleaching system involves the use of a mouth guard or tray within which the whitening agent is placed. The tray is then placed upon the teeth of the patient and of the tooth enamel and bleaching is allowed to take place. This method of treatment has the drawback of tooth sensitivity, possibly due to demineralization and irritation of oral tissues.

There is a demand in the marketplace for a tooth whitening dentifrice that can be used at home by the consumer which is safe and easy to use. A product for home use cannot utilize the ingredients for whitening teeth at the concentrations that are available for use by dental professionals, for as already discussed, the high concentration of bleaching agent can cause irritation of oral tissue.

There are available in the marketplace non-abrasive whitening dentifrice compositions for home use which contain 1–3% by weight concentrations of peroxide compounds which are somewhat effective when brushed on the teeth over a period of time. Such whitening dentifrices normally do not contain abrasive polishing agents such as silica and alumina compounds as such materials activate the rapid decomposition of the peroxide compound whereby the oxygen whitening agent is prematurely released. The gas evolution is especially undesirable with a toothpaste or gel product as such premature gas evolution can cause swelling and/or bursting of tubes containing these products. Capped tubes filled with dentifrice products containing peroxide compounds and silica abrasives have been known to explode within one day after filling. When alumina abrasives are substituted for silica, the filled product is pocketed with gas holes within days of filling.

A drawback to the use of peroxide whitening products for home use which are formulated without abrasives is that, in addition to having a slow whitening action, the products are not effective in stain removal. Thus, the polishing agent incorporated in a dentifrice acts to debride and physically scrub the external surface of teeth. This scrubbing action removes filmy bacterial and plaque layers as well as some of the stains and discoloring pigments that are found on teeth that cause the undesired discoloration. These polishing agents also microabrade the tooth so as to polish the teeth to give the enamel a more lustrous appearance and a higher optical sheen. This microabrasion action enhances the scrubbed teeth's ability to reflect white light and thereby appear brighter. Therefore there is a need in the marketplace for a home use dentifrice that provides enhanced whitening of teeth by effecting stain removal in addition to the whitening action of oxidizing peroxide.

SUMMARY OF THE INVENTION

The present invention encompasses a dual component dental whitening composition for home use which when applied to teeth contains a combination of a peroxide compound and an abrasive material normally incompatible with the peroxide compound whereby both heightened whitening and stain removal from teeth is attained.

The present invention is based upon the discovery that when a separately maintained peroxide dentifrice component and an abrasive containing dentifrice component which abrasive is normally incompatible with peroxide compounds are combined for the first time and applied to the surface of the teeth, an enhanced whitening effect is obtained, when the teeth are brushed, as a result of the combined presence of the peroxide and abrasive ingredients.

In one embodiment of the invention, a dual component dental whitening composition is provided which is comprised of separate urea peroxide and calcined alumina containing dentifrice components which are housed in a container wherein the components are maintained separate from each other and are not combined and admixed until simultaneous application to teeth is to be performed by the user as by brushing. Unexpectedly when the separately maintained dentifrice components are contacted with each other immediately prior to application to teeth, the ingredients contained in these components do not appreciably immediately react to decompose the urea peroxide and the combined dentifrice component composition will contain sufficient urea peroxide, in unreacted form, for a time sufficient, e.g., 1 to 10 minutes, to allow the peroxide, in its undecomposed, unreacted efficacious form, to be applied to the teeth simultaneously with a dentifrice component containing a normally incompatible abrasive material.

DESCRIPTION OF THE PREFERRED EMBODIMENTS

In the practice of the present invention the dentifrice component containing the peroxide ingredient is formulated using a vehicle containing a peroxide compound as the whitening agent, a chelating agent such as sodium ethylene diamine tetracetic acid and sodium acid pyrophosphate, and a thickener such as a polyoxyethylene/polyoxypropylene block copolymer.

Examples of suitable peroxide compounds used to prepare the whitening component of the present invention include metal ion free peroxide ingredients such as hydrogen peroxide and organic peroxides such as urea peroxide, glyceryl peroxide and benzoyl peroxide as well as metal ion containing peroxides such as calcium peroxide, and sodium percarbonate. A preferred peroxide compound is urea peroxide.

Typically, the peroxide compound is employed in the composition of the present invention in amounts so that at least about 0.5% by weight of the whitening component comprises a peroxide. Preferably, the peroxide compound comprises from about 1 to about 3% by weight of the whitening component.

Glycerin, and polyethylene glycol in combination with water are useful in formulating the vehicle for the whitening component dentifrice composition of the present invention. A combination of glycerine, polyethylene glycol and water is preferred as the vehicle in which the other ingredients of the peroxide component are contained.

Illustrative of polyethylene glycols useful in the practice of the present invention include polyethylene glycols known by the trademark Carbowax which are nonionic polymers of ethylene oxide having the general formula:

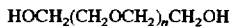
$HOCH_2(CH_2OCH_2)_nCH_2OH$ wherein n represents the average number of oxyethylene groups. The Carbowax polyethylene glycols are designated by a number such as 400, 600, 800, etc. which represents the average molecular weight. The average molecular weight of the polyethylene glycols used in the practice of the present invention is about 200–2000, preferably 400–800 and most preferably 600 (PEG 600).

Glycerin and polyethylene glycol are included in the peroxide dentifrice component of the present invention in an amount of from about 2 to about 20% by weight and preferably about 5 to about 15% by weight. Water is incorporated in the aqueous whitening dentifrice compositions of the present invention at a concentration of about 5 to about 30 by weight of the composition and preferably about 15 to about 25% by weight.

Thickening or gelling agents used in the formulation of the peroxide whitening dentifrice component include polyoxyethylene/polyoxypropylene block copolymers. Illustrative of polyoxyethylene/polyoxypropylene block copolymers useful in the practice of the present invention include block copolymers having the formula

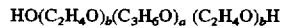
$HO(C_2H_4O)_b(C_3H_6O)_a(C_2H_4O)_bH$ wherein a is an integer such that the hydrophobic portion (moiety) represented by $(C_3H_6O)$ has a molecular weight of about 2750 to 4000. b is an integer such that the hydrophilic portion represented by $(C_2H_4O)$ constitutes about 70–80% by weight of the copolymer. Block copolymers of this composition are available commercially under the trademark Pluronic F type. Pluronic F127, which has a molecular weight of 4000 and contains 70% of the hydrophilic $C_2H_4O$ moiety is preferred in the practice of the present invention.

The thickening agent is preferably present in the peroxide dentifrice component in an amount within the range of about 1.0 to about 20% by weight and about 3 to 10% by weight is preferred.

Chleating agents used to prepare the peroxide dentifrice component include sodium acid pyrophosphate, disodium calcium ethylene diamine tetraacetic acid ($Na_2Ca$ EDTA), phosphoric acid, citric acid, sodium citrate, potassium citrate, sodium pyrophosphate, potassium pyrophosphate and disodium ethylenediamine tetraacetate. The chelating agent is incorporated in the peroxide containing dentifrice component of the present invention in an amount within the range of 0.1 to about 8.0% by weight and preferably about 0.5 to about 3.0% by weight.

If desired, an abrasive material such as a dicalcium phosphate abrasive, which is compatible with peroxide compounds, may be incorporated in the peroxide dentifrice component in accordance with the teachings of U.S. Pat. No. 5,171,564, which teachings are incorporated herein by reference. Examples of such dicalcium phosphate abrasives include dicalcium phosphate dihydrate and anhydrous dicalcium phosphate or calcium pyrophosphate. The dicalcium phosphate abrasive is advantageously incorporated in the peroxide dentifrice component at a concentration of about 10 to about 60% by weight and preferably about 20 to about 40% by weight.

The peroxide dentifrice component is normally applied to the teeth in the form of an aqueous gel. The peroxide gel may be prepared by suspending the peroxide ingredient in the vehicle heated to a temperature of 45° to 140° C. by mixing in any suitable mixer, such as a Lightening mixer for about 30 minutes until a homogeneous solution is formed. A substantially rigid, non-fluid gel product is obtained upon cooling.

The dentifrice component in which an abrasive material is included is generally prepared using a vehicle which contains water, humectant, surfactant and thickener.

The humectant is generally a mixture of humectants, such as glycerin, sorbitol and a polyethylene glycol of a molecular weight in the range of 200–1000, but other mixtures of humectants and single humectants may also be employed.

The humectant content is in the range of about 10% to about 80% by weight and preferably about 40 to about 50% by weight. The water content is in the range of about 10 to about 20% by weight.

Thickeners which may be used in the preparation of the abrasive component include natural and synthetic gums such as carrageenan (Irish moss), xanthan gum and sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose.

The thickener may be incorporated in the abrasive component dentifrice composition of the present invention at a concentration of about 0.1 to about 3% by weight and preferably about 0.5 to about 1% by weight.

Surface active agents are incorporated in the abrasive dentifrice component to provide foaming properties. The surface-active material is preferably anionic, nonionic or ampholytic in nature, and most preferably is anionic. Suitable examples of useful anionic surfactants are higher alkyl sulfates such as potassium or sodium lauryl sulfate which is preferred, higher fatty acid monoglyceride monosulfates, such as the salt of the monosulfated monoglyceride or hydrogenated coconut oil fatty acids, alkyl aryl sulfonates such as sodium dodecyl benzene sulfonate, higher fatty sulfoacetates, higher fatty acid esters of 1.2 dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the salts of N-lauroyl, N-myristoyl, or N-palmitoyl sarcosine.

The surface active agent is generally present at a concentration of about 0.5 to about 5.0% by weight of the present invention in the abrasive dentifrice component.

Abrasives which may be incorporated in the abrasive dentifrice component include siliceous materials, such as silica and alumina. A preferred silica is a precipitated amorphous hydrated silica, such as Sorbosil AC-35, marketed by Crossfield Chemicals, or Zeodent 115 from Huber Company. Alumina abrasives include alumina tri hydrate, aluminum silicate, calcined alumina and bentonite. Calcined alumina is a preferred alumina.

The concentration of abrasive in the abrasive dentifrice component of the present invention will normally be in the range of 15 to about 50% by weight and preferably 20 to 40% by weight.

Fluorine-providing salts having anti-caries efficacy may also be incorporated in the abrasive dentifrice component of the present invention and are characterized by their ability to release fluoride ions in water. Among these materials are inorganic metal salts, for example, sodium fluoride, potassium fluoride, a tin fluoride such as stannous fluoride or stannous chlorofluoride, sodium fluorosilicate, ammonium fluorosilicate and sodium monofluorophosphate. It is preferable to employ a fluoride salt to release about 10–1500 ppm of fluoride ion.

Synthetic anionic polymeric polycarboxylates optionally may be included in the abrasive dentifrice component. Polymeric polycarboxylates are well known, being often employed in the form of their free acids or preferably partially or more preferably fully neutralized water-soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether (maleic anhydride) having a molecular weight (M.W.) of about 30,000 to 1,000,000. These copolymers are available for example as Gantrez AN 139 (M.W. 500,000), AN 119 (M.W. 250,000) and preferably S-97 Pharmaceutical Grade of GAF Corporation. Other operative polymeric polycarboxylates include those disclosed in U.S. Pat. No. 3,956,480, such as the 1:1 copolymers of maleic anhydride with ethyl acrylate, hydroxyethyl methacrylate, N-vinyl-2-pyrrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates include those disclosed in U.S. Pat. No. 4,138,477, and U.S. Pat. 4,183,914, such as copolymers of maleic anhydride with styrene, isobutylene or ethyl vinyl ether, polyacrylic, polyitaconic and polymaleic acids, and sulfoacrylic oligomers of molecular weight as low as 1,000, available as Uniroyal ND-2.

Other ingredients which may be incorporated in the abrasive dentifrice component of the present invention include pigment, sweetener, flavor and preservative. In white dental cream formulations, the pigment will be titanium dioxide, rutile, and the proportion thereof will normally be in the range of 0.5 to 1% by weight, preferably 0.75 to 1.25% by weight. The sweetener content will normally be that of an artificial or synthetic sweetener and the normal proportion thereof present will be in the range of 0.1 to 1% by weight, preferably 0.3 to 0.5% by weight. The flavor content, which is preferably of a mixed peppermint/menthol flavor, will usually be in the range of 0.5 to 2% by weight, preferably 0.5 to 1.5% by weight. F.D. & C grade dyes may be used in appropriate amounts to provide desired colors.

Additional ingredients which may be incorporated in the abrasive dentifrice component of the present invention are antibacterial agents including noncationic antibacterial agents such as halogenated diphenyl ethers such as 2', 4, 4'-trichloro-2-hydroxy-diphenyl ether (Triclosan) and phenolic compounds including phenols, and their homologs, mono-and polyalkyl and aromatic halophenols, resorcinol and its derivatives, bisphenolic compounds and halogenated salicylanilides. Examples of other antibacterial agents which may be included in the abrasive dentifrice component include chlorhexidine, copper- and zinc- salts such as zinc citrate and sodium zinc citrate, sanguinarine extract, and metronidazole, quaternary ammonium compounds such as cetylpyridinium chloride, bis-guanides such as chlorhexidine digluconate, hexetidine, octenidine and alexidine.

The antibacterial agent is present in the abrasive dentifrice component in an effective antiplaque amount, typically 0.01–5% by weight, preferably about 0.03 to about 1% by weight.

Anti-inflammatory agents such as ibuprofen, flurbiprofen, aspirin, indomethacin etc. may also be included in the abrasive dentifrice component.

An anticalculus agent which is effective against calculus such as pyrophosphate salts including the mono, di, tri and tetra alkali metal and ammonium pyrophosphate and tripolyphosphate salts is still another additional ingredient which may be present in the abrasive component of the present invention . Such agents are used in amounts sufficient to reduce calculus and are preferably in amounts which will release about 1% by weight $P_2O_7$ ion and most preferably at least about 1.3% by weight $P_2O_7$ ion.

Plaque buffers such as calcium lactate, calcium glycerophosphate and stronthium polyacrylates may also be included in the abrasive component. Other optional ingredients include vitamins such as vitamin A, C, E, $B_6$, $B_{12}$, K, plant extracts as well as potassium salts useful in the treatment of dentin hypersensitivity such as potassium citrate, potassium chloride, potassium sulfate, potassium tartrate and potassium nitrate.

Peroxide activators such as manganese coordination complexes such as manganese gluconate may also be incorporated in the abrasive dentifrice component of the present invention. The activator compound when contacted with the peroxide ingredient of the peroxide dentifrice component activates the peroxide compound and accelerates the release of active oxygen to effect rapid whitening action. Other examples of manganese coordination complexes useful for incorporation in the abrasive dentifrice component as peroxide activators are described in copending application Ser. No. 08/499,532 filed Jul. 7, 1995, incorporated herein by reference. The manganese coordination complex compounds are included in the abrasive dentifrice component at a concentration of about 0.1 to about 3% by weight and preferably about 0.25 to about 1.75% by weight.

To prepare the abrasive dentifrice component of the present invention, the humectant and thickener are dispersed in a conventional mixer until the mixture becomes a slurry which is smooth in appearance, after which water is added. This mixture is heated to 100–100° F. and mixed for 10 to 30 minutes producing a homogeneous gel phase. Sweetener and color are added and mixed for 20 minutes. The mixture is transferred to a vacuum mixer and the abrasive is added and mixed for 10 to 30 minutes at high speed under a vacuum in the range of 5 to 100 millimeter of mercury pressure, preferably 5 to 50 mm Hg, providing a homogeneous mixture. The surfactant and flavor are then added to the paste which is followed by mixing another 10 to 20 minutes under vacuum of 5 to 50 mm Hg. The resultant product is an abrasive dentifrice paste of a texture like that of normal toothpastes having a pH in the range of 5 to 8, preferably 6.5 to 7.5, e.g., 7, and of satisfactory flavor.

Any convenient means for effecting the separation of the peroxide dentifrice component from the abrasive dentifrice component before being combined for use can be utilized. For example, a single container can be compartmentalized so that the peroxide containing dentifrice component and the abrasive containing component are housed in separate compartments and are not combined and admixed until extrusion from the dual compartment container and application to the teeth. Alternatively, the peroxide containing component and the abrasive containing component can be housed in separate containers from which the respective components are dispensed together and combined just prior to use.

The following examples are further illustrative of the present invention, but it is understood that the invention is not limited thereto. All amounts and proportions referred to herein and the appended claims are by weight.

EXAMPLE 1

Peroxide Dentifrice Component

A peroxide dentifrice useful as a component of the dual component whitening dentifrice of the present invention was prepared with the following ingredients.

| Ingredients | Wt. % |
| --- | --- |
| Urea peroxide | 6.60 |
| Calcium pyrophosphate | 27.50 |
| Deionized H$_2$O | 21.68 |
| Pluronic F-127 | 17.0 |
| Glycerin | 12.50 |
| PEG-600 | 12.50 |
| Sodium acid pyrophosphate | 2.00 |
| Citric Acid | 0.2 |
| Na$_2$CaEDTA | 0.04 |

The peroxide dentifrice component was prepared in a Ross mixer. Water, citric acid, glycerin, and PEG 600 were mixed for 10 minutes at low speed without vacuum. Pluronic F-127 was added and the mixture stirred for 30 minutes without vacuum and then an additional 30–45 minutes with vacuum of -15 mmHg. Na$_2$H$_2$EDTA, calcium pyrophosphate, and sodium acid pyrophosphate, were added and mixed for 15–20 minutes with vacuum. Then, urea peroxide was added and mixed for 10–15 minutes under vacuum. The resulting product was a paste.

Abrasive Dentifrice Component

An abrasive dentifrice useful as a component of the dual component dentifrice of the present invention was prepared with the following ingredients:

| Ingredient | Wt. % |
| --- | --- |
| Sorbitol | 15.0 |
| Glycerin | 15.0 |
| Silica (Zeodent 115) | 15.0 |
| Alumina (Calcined) | 20.0 |
| Deionized water | 20.75 |
| Polyethylene Glycol 600 | 3.0 |
| Anionic Polycarboxylate (Gantrez S-97) | 2.0 |
| Sodium lauryl sulfate | 1.8 |
| Sodium Monofluro/phosphate | 1.52 |
| Carboxymethyl cellulose | 0.8 |
| Sodium saccharin | 0.6 |
| TiO$_2$ | 0.3 |
| Flavor | 2.4 |

The glycerin, sorbitol, polyethylene glycol, carboxymethyl cellulose were dispersed in a conventional mixer until the mixture became a slurry, which was smooth in appearance, water was added and mixed for 10 to 30 minutes producing a homogeneous gel phase in which the sodium monofluorophosphate and Gantrez was dispersed. Color and sweetener were added mixed for 20 minutes and transferred to a vacuum mixer. The alumina, silica and TiO$_2$ were then added and mixed for 10 to 30 minutes at high speed under a vacuum of about 50 mm Hg, providing a homogenous mixture. The sodium lauryl sulfate and flavor were then added to the paste which was followed by mixing another 20 minutes under vacuum of 50 mm Hg. The resultant product was a toothpaste with satisfactory flavor.

The peroxide and abrasive dentifrice components prepared above were of extrudable consistency. After 21 days of storage in separate containers, separate ribbons of the two dentifrice components were extruded sequentially onto the bristles of a toothbrush. T en minutes after the two dentifrice ribbons were combined, the mixture was analyzed for peroxide content. Analysis indicated the presence of 1.3% 02, as hydrogen peroxide, indicating that 88% of the urea peroxide originally incorporated in the peroxide dentifrice component was available for whitening.

To determine the stain removal efficacy of the combined dual components, extracted human molars having a high degree of discoloration were exposed for 6 hours at 37° C. to a slurry of the combined dentifrice components to determine the whiteness of the teeth. The slurry was prepared by mixing 1 part of the combined peroxide and abrasive dentifrice components of Example 1 with 2 parts distilled water.

Before the discolored teeth were exposed to the slurry of combined dentifrice components, the color of the teeth to undergo treatment was measured with a Minolta Chroma Meter using values obtained from the CIE (Commission Inter national D'Eclairage) L*, a* and b* scale. This scale represents the mathematical approximation of the non-linear response of the eye to light. A zero value for a* and b* means some shade of gray. Positive values for a* and b* indicate redness and yellowness. Negative a* an d b* represents values for green and blue.

After the 6 hour exposure time, the color of the teeth was again measured. The increase in whiteness was calculated using the equation:

$$\text{delta } E = \sqrt{(\text{delta } L^*)^2 + ((\text{delta } a^*)^2 + (\text{delta } b^*)^2)}$$

where delta E represents an increase in whiteness. Delta L*, delta a* and delta b* represent the changes that have occurred in these parameters after treatment with the slurry combined components.

The change in stain scores of the treated teeth is recorded in Table I below for purposes of comparison, the procedure of Example 1 was repeated using slurries of commercially available toothpastes sold for whiteing teeth which were purchased on the open market. The slurries were prepared by mixing one part toothpaste with two parts distilled water. The first of these commercial whitening toothpastes contained 25% silica and was designated "Composition 2". A second commercially available whitening dentifrice which contained 8% hydrated alumina was designated "composition 3". The results obtained with comparative Compositions 2 and 3 are also recorded in Table I below.

TABLE I

Extrinsic Stain Removed By Dentifrice Formulations
delta L*, delta a* · delta b*, delta E scores

| Dentifrice Composition | Change in Extrinsic Stain Scores | | | |
| --- | --- | --- | --- | --- |
| | delta L* | delta a* | delta b* | delta E* |
| 1 | 18.99 ± 4.23 | −3.76 ± 1.10 | 0.19 ± 2.63 | 19.56 ± 4.20 |
| 2 | 14.06 ± 3.30 | −2.86 ± 0.83 | 0.23 ± 1.98 | 14.50 ± 3.29 |
| 3 | 10.73 ± 1.74 | −2.57 ± 0.87 | 1.02 ± 2.71 | 11.40 ± 1.82 |

The scores recorded in Table I indicate that when extracted human molars are exposed to a slurry of the dual component composition of the present invention (Composition 1) a level in whiteness is achieved which on average is 35–72% higher than teeth exposed to slurries of commercial toothpaste compositions sold for tooth whitening purposes (Compositions 2 and 3).

EXAMPLE II

The tooth polishing efficacy of the dual component dentifrice of Example I was determined in accordance with the enamel polish test procedure described below:

Enamel Polishing Test Procedure

Enamel polish was determined using eight replicate extracted bovine incisors that were chemically dulled by immersion in 10 ml 0.2M HCl and then polished with a slurry of the combined dual component dentifrice prepared by mixing 1 part of the combined dentifrice with 2 parts distilled water. The teeth were polished with a toothbrush using an automatic toothbrushing machine which stroked the teeth with the dentifrice slurry at a position perpendicular to the longitudinal axis of the teeth. After 2000 strokes were applied to the teeth at a pressure on the brush of 300 grams, the degree of polish was determined with a reflectometer that measured the intensity of spectral light reflected by the treated teeth specimens. The greater the intensity of the reflected light from a specimen, the higher is the luster of the teeth and consequently the higher is the numerical polish score.

The reflectance scores obtained from the chemically dulled teeth before polishing, which served as a baseline, as well as the reflectance scores obtained after polishing with Composition 1 of Example I are recorded in Table II below. For purposes of comparison, the reflectance scores obtained at baseline and after polishing with comparative Compositions 2 and 3 are also recorded in Table II below.

TABLE II

Tooth Polish Scores Produced By Dentifrice Slurries

| Dentitrice Composition | Reflectance Baseline Score Before Polishing | Reflectance Score After Polishing |
| --- | --- | --- |
| 1 | 18 ± 2 | 77 ± 6 |
| 2 | 18 ± 2 | 49 ± 5 |
| 3 | 18 ± 2 | 40 ± 3 |

The reflectance scores recorded in Table II indicate that Composition 1 outperformed the commercially available whitening dentifrices Compositions 2 and 3. The difference in scores was statistically significant ($p<0.05$).

What is claimed is:

1. A method for whitening teeth which comprises preparing a first dentifrice component comprising a peroxide compound and a second dentifrice component which is free from any peroxide compound and comprises an abrasive combination of a silica and alumina which is incompatible with the peroxide and which activates rapid decomposition and gas evolution of the peroxide compound, the first dentifrice component being free of any silica or alumina abrasive, maintaining the first and second dentifrice components separate from the other in separate compartments its of a multicompartmented container, simultaneously extruding and combining the separate components from the separate compartments and thereafter applying the combined components to the teeth to effect heightened whiteing of the teeth.

2. The method of claim 1 wherein the peroxide is urea peroxide.

3. The method of claim 1 wherein a peroxide activator is present in the abrasive dentifrice component in an amount effective to activate the peroxide compound in the peroxide dentifrice component when the two components are combined for use.

4. The method of claim 3 wherein the activator is a manganese coordination complex compound.

5. The method of claim 1 wherein the manganese coordination complex compound is manganese gluconate.

6. The method of claim 1 wherein an antibacterial agent is present in the abrasive dentifrice component.

7. The method of claim 6 wherein the antibacterial agent is Triclosan.

8. The method of claim 1 wherein a potassium salt effective in the treatment of dentin hypersensitivity is present in the abrasive dentifrice component.

9. The method of claim 8 wherein the potassium salt is potassium nitrate.

10. The method of claim 1 wherein a vitamin compound is present in the abrasive dentifrice component.

11. The method of claim 1 wherein the vitamin compound is vitamin C.

12. A container containing an aqueous tooth whitening composition, the container having two compartments for separate storage of dentifrice components containing incompatible ingredients of the composition, the components being adapted to be simultaneously extruded from the compartments and combined without substantial reaction with each other, the first compartment housing a dentifrice component comprising a peroxide compound and the second compartment housing a dentifrice component which is free of any peroxide compound and comprises an abrasive combination of silica and alumina which is incompatible with the peroxide compound and which activates rapid decomposition and gas evolution of the peroxide compound, the first dentifrice component being free of any silica or alumina abrasive, the combined dentifrice components when extruded and combined and thereafter applied to teeth to effect heightened whitening of the teeth.

13. The container of claim 12 wherein the peroxide compound is hydrogen peroxide.

14. The container of claim 12 wherein the peroxide compound is urea peroxide.

15. The container of claim 12 wherein the alumina is calcined alumina.

16. The container of claim 12 wherein there is included in the abrasive containing second component a peroxide activator.

17. The container of claim 16 wherein the peroxide activator is a manganese coordination complex compound.

18. The container of claim 17 wherein the manganese coordination complex is manganese gluconate.

19. The container of claim 12 wherein an antibacterial agent is included in the second abrasive containing dentifrice component.

20. The composition of claim 19 wherein the antibacterial agent is Triclosan.

21. The composition of claim 1 wherein a potassium salt effective in the treatment of dentin hypersensitivity is included in the second abrasive component.

22. The composition of claim 21 wherein the potassium salt is potassium nitrate.

23. The composition of claim 12 wherein a vitamin compound is present in the abrasive dentifrice component.

24. The composition of claim 23 wherein the vitamin compound is vitamin C.

* * * * *